(12) United States Patent
Hasegawa

(10) Patent No.: US 12,070,402 B2
(45) Date of Patent: Aug. 27, 2024

(54) STENT DEVICE WITH STENT COVERING HAVING PLURALITY OF BONDING AREAS

(71) Applicant: OLYMPUS CORPORATION, Tokyo (JP)

(72) Inventor: Mamoru Hasegawa, Kamiina-gun (JP)

(73) Assignee: Olympus Corporation, Tokyo (JP)

( * ) Notice: Subject to any disclaimer, the term of this patent is extended or adjusted under 35 U.S.C. 154(b) by 53 days.

(21) Appl. No.: 17/673,690

(22) Filed: Feb. 16, 2022

(65) Prior Publication Data

US 2022/0313461 A1 Oct. 6, 2022

Related U.S. Application Data

(60) Provisional application No. 63/168,370, filed on Mar. 31, 2021.

(51) Int. Cl.
*A61F 2/90* (2013.01)
*A61F 2/07* (2013.01)
*A61F 2/844* (2013.01)
*A61F 2/848* (2013.01)
*A61F 2/95* (2013.01)
*A61F 2/966* (2013.01)
*A61F 2/04* (2013.01)

(52) U.S. Cl.
CPC .................. *A61F 2/90* (2013.01); *A61F 2/07* (2013.01); *A61F 2/844* (2013.01); *A61F 2/848* (2013.01); *A61F 2/9517* (2020.05); *A61F 2/966* (2013.01); *A61F 2/04* (2013.01); *A61F 2002/072* (2013.01); *A61F 2002/075* (2013.01)

(58) Field of Classification Search
CPC .......... A61F 2/90; A61F 2/9517; A61F 2/844; A61F 2/848; A61F 2/966; A61F 2/07; A61F 2002/072; A61F 2002/075; A61F 2/04

See application file for complete search history.

(56) References Cited

U.S. PATENT DOCUMENTS

| | | | | |
|---|---|---|---|---|
| 5,667,523 A | * | 9/1997 | Bynon ..................... | A61F 2/91 606/198 |
| 5,693,085 A | * | 12/1997 | Buirge ..................... | A61F 2/91 623/1.13 |
| 5,843,158 A | * | 12/1998 | Lenker ..................... | A61F 2/90 623/1.13 |

(Continued)

FOREIGN PATENT DOCUMENTS

| | | | |
|---|---|---|---|
| JP | 6317826 | B2 | 4/2018 |
| JP | 6350924 | B2 | 7/2018 |
| JP | 6355115 | B2 | 7/2018 |

*Primary Examiner* — Jing Rui Ou

(74) *Attorney, Agent, or Firm* — Morgan, Lewis & Bockius LLP

(57) ABSTRACT

Stent device has a stent cover bonding to the stent wires forming the stent body at a plurality of bonding portions that are remote from the cross over points of the stent wire. By allocating the bonding portions to the stent wires in between the cross over portions, the axial flexibility of the stent device is maintained. The stent cover bonded by the disclosed bonding portions contributes to preventing lumen tissues to penetrate into the stent body and clogging the stent while placement of the bonding portions bonding the stent cover to the stent device provides variations of positive effects to the cover stent device and to the patient in which the stent device is placed.

23 Claims, 11 Drawing Sheets

(56) References Cited

U.S. PATENT DOCUMENTS

| | | | | |
|---|---|---|---|---|
| 6,010,529 | A * | 1/2000 | Herweck | C08L 27/18 623/23.69 |
| 2002/0147489 | A1 * | 10/2002 | Hong | A61F 2/90 623/1.2 |
| 2002/0198588 | A1 * | 12/2002 | Armstrong | A61F 2/07 623/1.13 |
| 2003/0181968 | A1 * | 9/2003 | Xie | A61F 2/07 623/1.13 |
| 2005/0222667 | A1 * | 10/2005 | Hunt | A61F 2/07 623/1.13 |
| 2007/0112411 | A1 * | 5/2007 | Obermiller | A61L 27/3629 623/1.13 |
| 2010/0228335 | A1 * | 9/2010 | Schorgl | A61L 31/08 623/1.42 |
| 2012/0101563 | A1 * | 4/2012 | Zhu | A61F 2/966 623/1.12 |
| 2013/0226282 | A1 * | 8/2013 | Ahn | B22D 11/005 29/527.5 |
| 2013/0306232 | A1 * | 11/2013 | Hedberg | B32B 38/0004 156/250 |
| 2017/0014133 | A1 | 1/2017 | Han et al. | |
| 2017/0049589 | A1 | 2/2017 | Han et al. | |
| 2017/0143467 | A1 | 5/2017 | Myung | |
| 2018/0263626 | A1 | 9/2018 | Han et al. | |
| 2019/0142615 | A1 | 5/2019 | Han et al. | |

\* cited by examiner

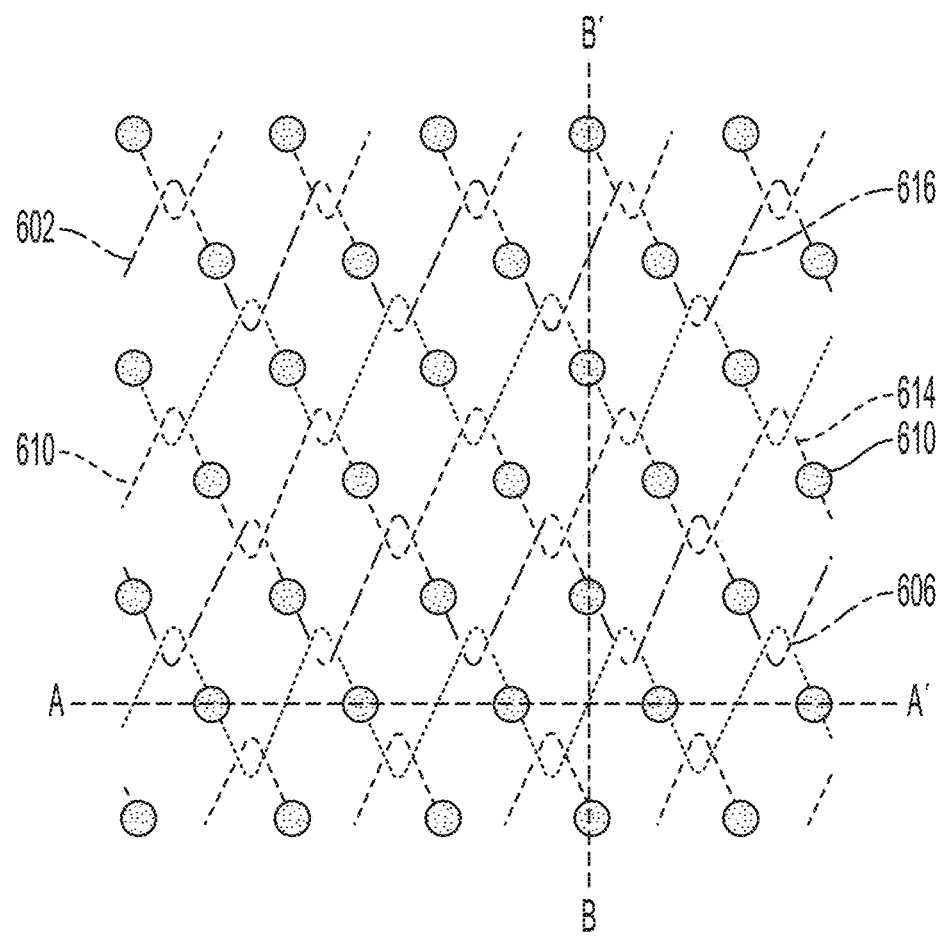
FIG. 8A
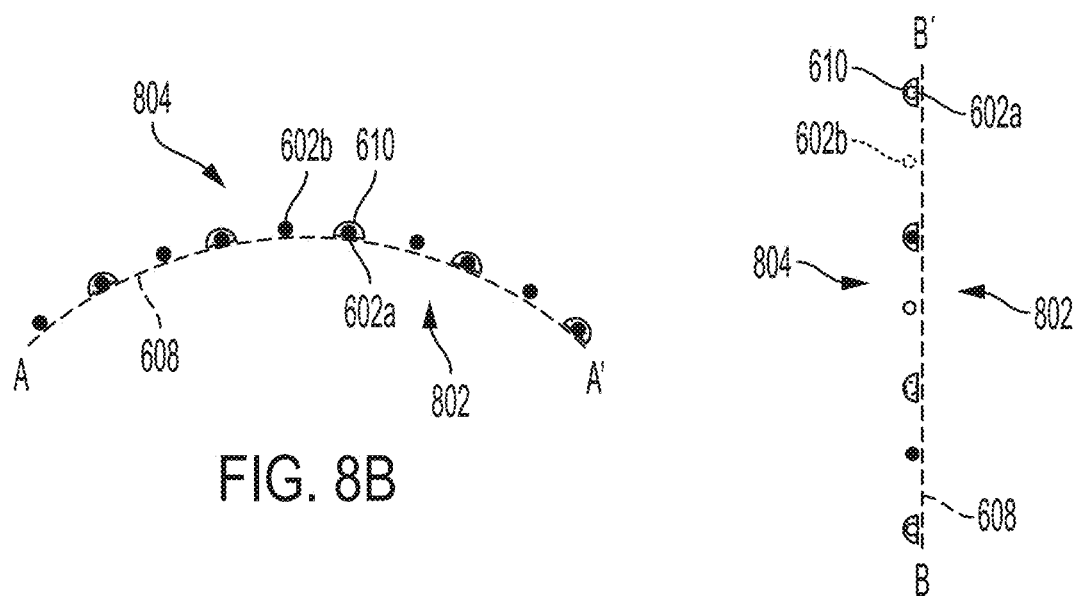
FIG. 8B
FIG. 8C

STENT DEVICE WITH STENT COVERING HAVING PLURALITY OF BONDING AREAS

RELATED APPLICATION DATA

This application is based on and claims priority under 35 U.S.C. § 119 to U.S. Provisional Application No. 63/168,370 filed on Mar. 31, 2021, the entire contents of which are incorporated herein by reference.

FIELD OF DISCLOSURE

The present invention relates generally to stent devices and, in particular, to a stent device having a stent cover bonded to the stent body through a plurality of bonding areas, which contributes to increased axial flexibility of the stent device, particularly in areas of looping, interlocking, and/or entanglement between the wires forming the stent body.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

In general, stent devices are implanted in the internal organs of a patient so as to push the lesion site and widen the stenosed organ such as vascular, bile duct, esophagus, duodenum, and intestines. Stent devices may be covered or uncovered. On the one hand, in uncovered stent devices, restenosis may occur after implantation as lumen cells enter the stent lumen through the mesh of wires ("ingrowth"). While restenosis which may help to anchor a stent device and prevent the uncovered stent device from migration, i.e., shifting its position within the patient, restenosis may lead to a return of or new unwanted medical conditions, such as hyperplasia of lumen tissue into the inner luminal side of the stent body. On the other hand, as a measure against restenosis, covered stent devices may be used. But while the cover of covered stent devices prevents restenosis, the cover may also decrease axial flexibility of the stent device, which may be required in case the stent device needs to be implanted to internal organs and its lumens having complex shape.

FIG. 13 is a figure of a covered stent device disclosed in the related art (U.S. Pat. Pub. No. 2017/0143467A1). FIG. 13 is a partial cross-sectional view showing an inside structure of the related art covered stent 100. The related art cover stent 100 is comprised of a cylindrical stent body 52 and a stent cover formed by PTFE tape 10-1 and PTFE tape 10. The cylindrical stent body 52 is formed by weaving different shape-memory alloy wires 1 and 2 alternatively with a plurality of interlocking portions 3 and a plurality of intersection portions 4 such that rhombic openings 5 are changeable in size by external force. The PTFE tape 10-1 is placed, e.g., wound, over the entire outer surface of the cylindrical stent body 52 and PTFE tape 10 is placed intermittently on the inside surface of the cylindrical stent body 52. Upon applying heat and pressure to the entire stent device, the PTFE tape 10-1 and PTFE tape 10 are bonded to each other through the rhombic openings 5, whereas the PTFE tape 10-1 that did not bond with the PTFE tape 10 due to the intervals of placement of PTFE 10 remains free relative to the cylindrical stent body 52. This configuration allows the related art covered stent 100 to be covered entirely by PTFE tape 10-1 from the outer surface preventing invasion of the lesion into the cylindrical stent, and at the same time, enables axial flexibility due to the bonding intervals of the PTFE tape 10-1 and PTFE tape 10. FIG. 14 is a figure from the same related art (U.S. Pat. Pub. No. 2017/0143467A1) and is a photograph showing the bending characteristics of an actual product of the related art covered stent 100.

Although the related art covered stent 100 has a certain amount of flexibility and axial force, the location of the bending portion is fixed to the intervals of the PTFE tape 10, which may not coincide with the location within the lumen of the internal organs at which the bending needs to occur. Moreover, in case that the covered stent is comprised of plurality of interlocking portions 3 where one or more wire is entangled, the covered stent may unexpectedly lose flexibility if the PTFE tap 10 covers the area including certain interlocking portions 3. As a result, the therapeutic effect may be reduced due to the face that the related art covered stent 100 does not fit the shape of the lumen in which it is placed.

SUMMARY

Accordingly, there is a need for a covered stent device with a structure that, in view of the practical usage, would substantially obviate one or more of the issues due to limitations and disadvantages of related art covered stent device. An object of the present disclosure is to provide an improved stent device having an efficient structure and practical administration of the associated medical procedure. Additionally, there is a need for an improved covered stent device that balances the risks of restenosis and migration while allowing the stent device to serve its purpose of widening the stenosed organ at the treating portion through flexibly reaching the treatment portion. At least one or some of the objectives is achieved by the stent device disclosed herein.

In general, the disclosed structures and systems provide for a stent and stent cover efficiently suppressing problems such as ingrowth discussed above and in relation with the related art. To address the issues, a structure where a stent cover bonding with the stent wires at locations other than the interlocking structures of the stent wires is disclosed.

For example, the disclosed stent device has a stent cover that bonds to the stent body at portions of the stent wires (which from the stent body) other than at location of the interlocking structure of the stent wires (the interlocking structure of the stent wires being one of an primary interlocking structure such as a loop structure or a second interlocking structure such as an intersecting structure where a first wire crosses or passes over/under a second wire). Separating the location of the bonding between stent cover and stent body from the location of the interlocking structure of the stent wires (whether a primary interlocking structure or a secondary interlocking structure) maintains the flexibility of the covered stent device while at the same time preventing growth and hyperplasia of lumen tissues to protrude into the inner luminal side of the stent device, which may cause clogging of the stent device. The stent wires woven into the stent body of the stent device may be separated into two types, stent wires closer to the inner lumen of the stent device and stent wires closer to the space that is exterior of the stent device. The stent wires to which the stent cover bonds is based on the placement of the stent cover—the stent wires closer to the inner lumen of the stent device bond with the stent cover placed on the surface of the stent body oriented toward the inner lumen of the stent device and the stent wires closer to the space exterior of the stent device bond with the stent cover placed outside of the outer surface of the stent body.

In some aspects, the bonding of the stent cover and the stent wires may occur in multiple locations along a length of a stent wire between the interlocking structures of the stent body. The bonding of the stent cover and stent wires may occur at distinct points or at certain lengths, in accordance with the level of flexibility to be maintained. The stent cover may fold back at both ends of the stent device and be adhered together in order to form a fixed portion for firmly fixing the stent cover to the stent device.

Embodiments of the disclosed stent device comprises one or more stent wires forming a stent body that encloses an interior void space and defines an inner luminal surface of the stent body and a stent cover covering at least one part of the stent body. The one or more stent wires of the stent body consist of cross over points forming a plurality of open cells in which each open cell includes a perimeter defined by a portion of the one or more stent wires and enclosing a cell void space. The stent cover and a first section of the portion of the one or more stent wires are bond together at a bonding portion and the cross over points and the bonding portion are separated from each other by a second section of the portion of the one or more stent wires, the second section not bonded to the stent cover.

Embodiments of the disclosed stent device further comprises a single bonding portion that is present on the first section of the portion of the one or more stent wires between adjacent cross over points.

Embodiments of the disclosed stent device further comprises multiple bonding portions that are present on the first section of the portion of the one or more stent wires between adjacent cross over points.

Embodiments of the disclosed stent device further comprises bonding portions that are present on up to 80% of a total length the first section of the portion of the one or more stent wires between adjacent cross over points bonding portions.

Embodiments of the disclosed stent device further comprises stent cover that is located on the inner lumen surface of the stent body.

Embodiments of the disclosed stent device further comprises stent cover extending the entire axial length of the stent body.

Embodiments of the disclosed stent device further comprises stent cover that is folded back to cover an end portion of the inner lumen surface of the stent body.

Embodiments of the disclosed stent device further comprises a bonding portions that is located on an inner wire portion of the stent wire, the inner wire portion of the stent wire being radially inward from an outer wire portion of the stent wire.

Embodiments of the disclosed stent device further comprises stent cover that is located on an outer surface of the stent body.

Embodiments of the disclosed stent device further comprises stent cover extending the entire axial length of the stent body.

Embodiments of the disclosed stent device further comprises stent cover that is folded back to cover an end portion of the outer surface of the stent body.

Embodiments of the disclosed stent device further comprises a bonding portion that is located on an outer wire portion of the stent wire, the outer wire portion of the stent wire being radially outward from an inner wire portion of the stent wire.

Embodiments of the disclosed stent device further comprises stent cover including a first stent cover portion located on the inner lumen surface of the stent body and a second stent cover portion located on an outer surface of the stent body.

Embodiments of the disclosed stent device further comprises at least one of the first stent cover portion and the second stent cover portion extending the entire axial length of the stent body.

Embodiments of the disclosed stent device further comprises both the first stent cover portion and the second stent cover portion extending the entire axial length of the stent body.

Embodiments of the disclosed stent device further comprises stent cover that is folded back to cover an end portion of the outer surface of the stent body.

Embodiments of the disclosed stent device further comprises the first stent cover portion and the second stent cover portion that are bonded together at the plurality of open cells.

Embodiments of the disclosed stent device further comprises the bonding portion including a first bonding portion located on an inner wire portion of the stent wire and a second bonding portion located on the outer wire portion of the stent wire, wherein the inner wire portion of the stent wire is radially inward from the outer wire portion of the stent wire.

Embodiments of the disclosed stent device further comprises the cross over points including a primary interlocking structure.

Embodiments of the disclosed stent device further comprises the cross over points including a secondary interlocking structure.

Embodiments of the disclosed stent device further comprises a stent delivery system, comprising a tip, the covered stent device, a double layered sheath having an axial length and configured to carry the covered stent device from a first position along the axial length to a second position along the axial length, and a handle for removing the stent device from the double layered sheath.

The term "patient," as used herein, comprises any and all organisms and includes the term "subject." A patient can be a human or an animal.

Additional features and advantages will be set forth in the description that follows, and in part will be apparent from the description, or may be learned by practice of the invention. The objectives and other advantages of the disclosed stent device will be realized and attained by the structure particularly pointed out in the written description and claims thereof, as well as the appended drawings.

Other systems, methods, features and advantages will be, or will become, apparent to one with skill in the art upon examination of the following figures and detailed description. It is intended that all such additional systems, methods, features and advantages be included within this description, be within the scope of the present disclosure, and be protected by the following claims. Nothing in this section should be taken as a limitation on those claims. Further aspects and advantages are discussed below in conjunction with the embodiments of the disclosed input device. It is to be understood that both the foregoing general description and the following detailed description of the disclosed input device are examples and explanatory and are intended to provide further explanation of the disclosed stent device as claimed.

BRIEF DESCRIPTION OF THE DRAWING

The following detailed description of preferred embodiments can be read in connection with the accompanying drawings in which like numerals designate like elements and in which:

FIGS. 8A to 8C are magnified schematic views of embodiments of a stent body and showing aspects of the stent wires.

Figure 1:
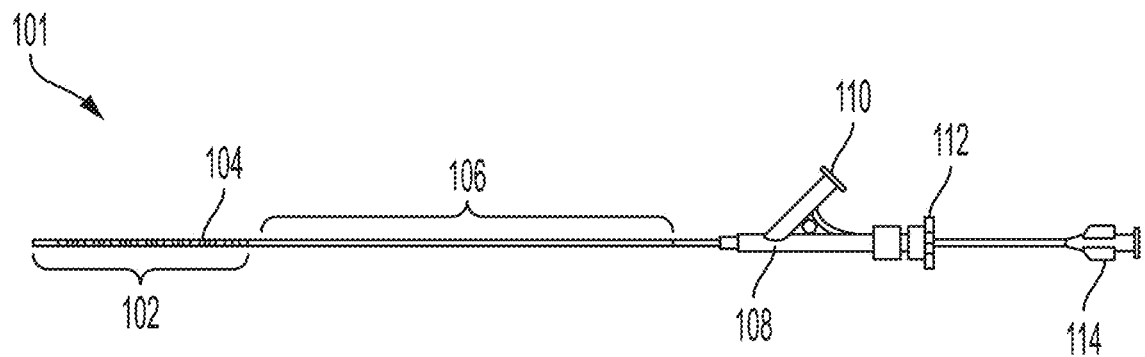
FIG. 1 illustrates an embodiment of a stent delivery system including the stent device.

Throughout all of the drawings, dimensions of respective constituent elements are appropriately adjusted for clarity. For ease of viewing, in some instances only some of the named features in the figures are labeled with reference numerals.

DETAILED DESCRIPTION

FIG. 1 is an illustration of a stent device delivering system 101. Stent delivery system 101 is comprised of tip portion 102, the stent device 104, sheath 106, two port hub 108, side port 110, rotatable handle lock 112, inner handle 114. The sheath 106 has a two-layered structure with inner sheath and outer sheath, having the stent device 104 in a reduced diameter held between the two layers at the tip portion 102. The tip portion 102 is connected to the inner sheath and the inner handle 114. The outer sheath is connected to the two port hub 108 and rotatable handle lock 112. After the stent delivery system 101 places the tip portion 102 and the stent device 104 to the desired position, by fixing the inner handle 110 and pulling the rotatable handle lock 112 toward the proximal side of the delivery system 101, the outer sheath at the tip portion 102 slides toward the proximal side, causing the stent device 104 to self-expand from the reduced diameter to the designed diameter. After the outer sheath finishes sliding the entire length of the stent device 104, the delivery system 101 and the stent device 104 are separated, leaving the stent device 104 to be implanted in the patient's body.

In some procedures, the stent delivery system 101 implants the stent device 104 into the patient's body to open stenosis (e.g., vascular (circulatory) stents) and, in some embodiments, the procedures are combined with the use of an endoscope. For example, in the case for implanting bile duct stents, the endoscope is inserted through the mouth and advanced to the duodenum. Then the stent delivery system 101 is inserted through the forceps channel of the endoscope and through the duodenal papilla into the bile duct. Finally, the stent device 104 is placed in the bile duct stenosis with supports from visual imagery from the endoscope.

Figure 2A:
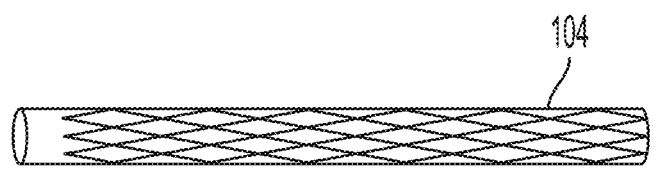
FIGS. 2A and 2B show schematic views of the stent body in a collapsed state (FIG. 2A) and in an expanded state (FIG. 2B).
Figure 2B:
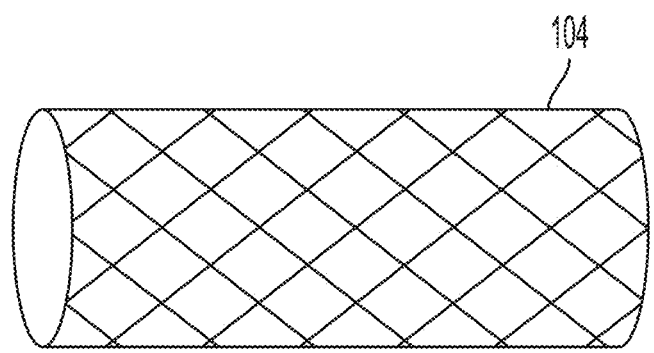

FIG. 2A is an illustration of the stent device 104 with the stent body in its contracted state. The extent of the axial shortening occurring as the stent body contracts is dependent on the interlocking structures of the stent wires. The stent device is inserted into the stent delivery system 101 in the contracted state in order for the delivery of the stent device 104 to occur through blood vessels of the patient and other narrow spaces. As disclosed in FIG. 2B, after the stent device 104, which is a self-expandable stent, reaches the treating portion and is pushed out from the stent delivery system 101, the stent device 104 expands into the size it was designed for conducting treatment to the treating portion.

Figure 3:
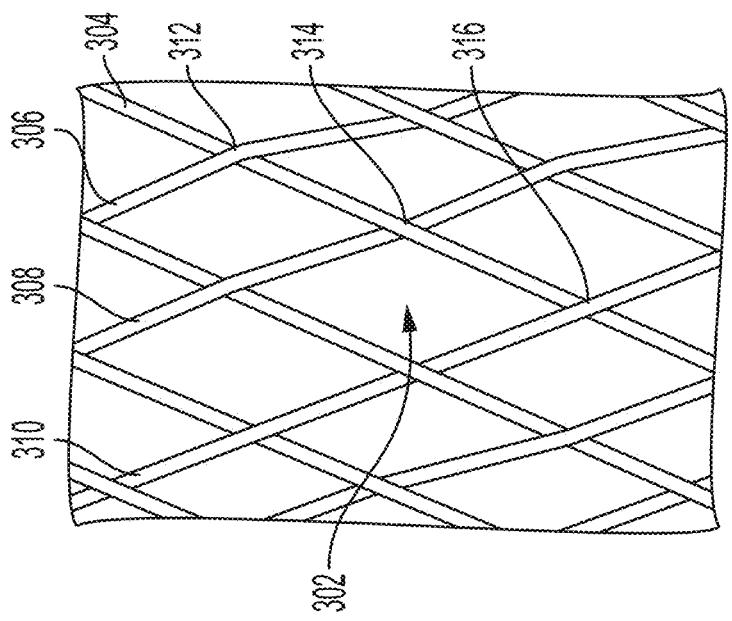

FIG. 3 illustrates a pattern of the stent wires comprising the stent body of the stent device 104. As disclosed in FIG. 3, the stent wires cross over each other and form cells enclosed by the stent wires, such as stent cell 302. The interconnection or overlap of the stent wires can be seen in FIG. 3 by, for example, observing the positional relationship of stent wire 304 as it intersects with stent wires 306, 308, and 310. The stent wire 304 intersects with stent wire 306 at intersection 312, where stent wire 304 goes under stent wire 306. The stent wire 304 then intersects with stent wire 308 at intersection 314, where stent wire 304 goes over stent wire 308. Then stent wire 304 goes under stent wire 310 at the next intersection 316. The alternating under and over location of wire 304 with respect to intersecting wires at each intersection repeats throughout the stent body shown in FIG. 3.

Figure 4:
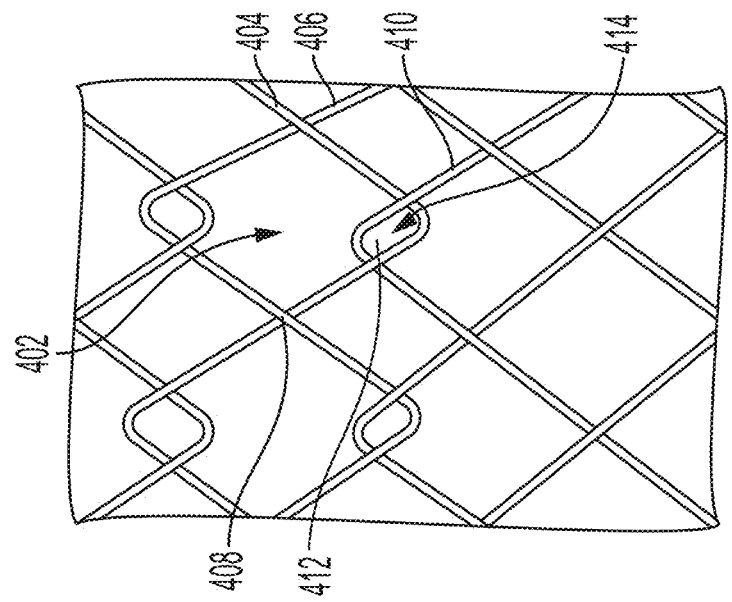
FIGS. 3 and 4 are magnified views of embodiments of a stent body and showing aspects of the stent wires.

FIG. 4 illustrates another pattern of the stent wires comprising the stent body of the stent device 104. As with FIG. 3, the stent wires of the stent device 104 cross over each other and form cells enclosed by the stent wires, such as stent cell 402. The interconnection or overlap of the stent wires in the stent body shown in FIG. 4 is more complex compared to that in FIG. 3. For example, the stent wires 404 and 406 cross over each other at intersection 408, but each of stent wires 404 and 406 bend and form an interlocking structure with a respective further stent wire, such as stent wires 404 and 410 forming an interlocking intersection 412. Because stent wires 404 and 410 can move independent of each other, stent wires 404 and 410 in the region of interlocking intersection 412 can form an interlocking stent cell 414.

The stent device 104 can be made by weaving NiTi alloy wires or other wires made from biocompatible materials. The tubular shape is memorized when the stent device 104 is expanded into a tubular shape.

Figure 5:
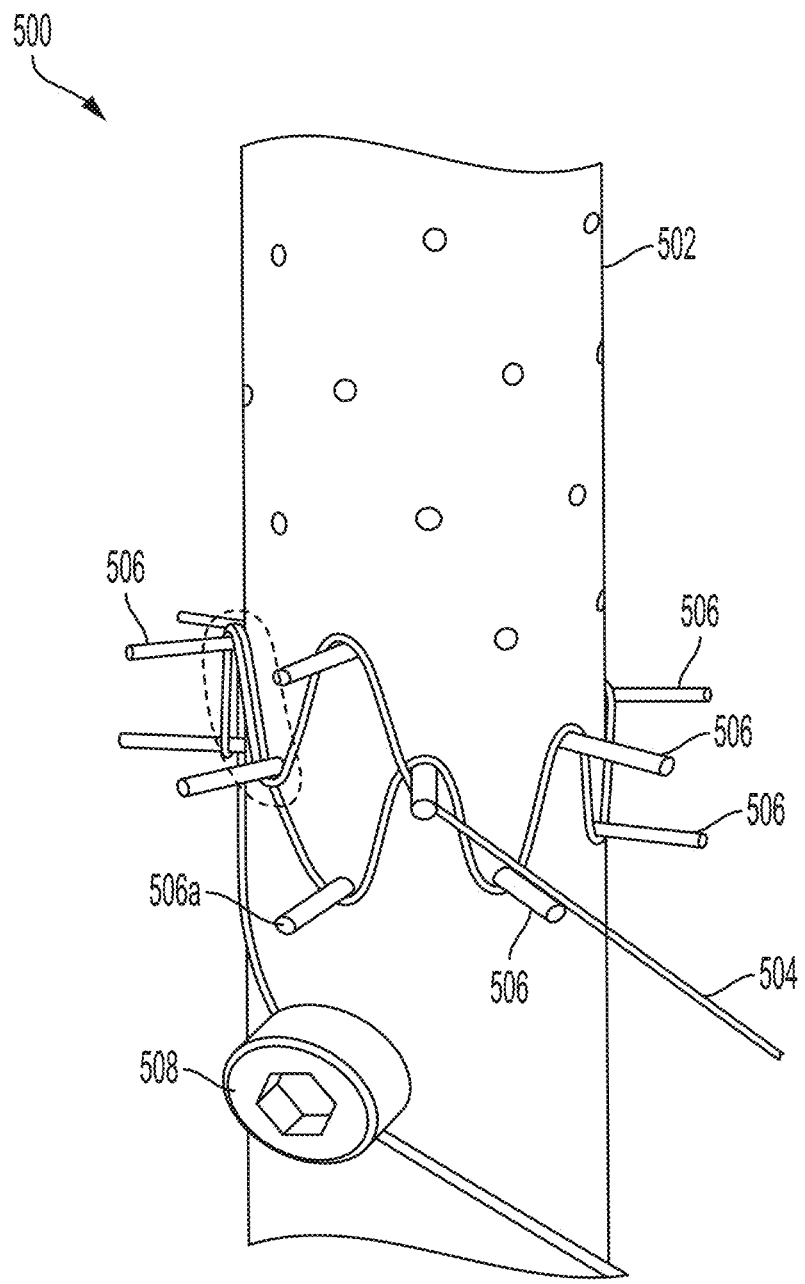
FIG. 5 illustrates examples of a method for manufacturing of the stent device.

FIG. 5 illustrates an example of a method for manufacturing of the stent device. The method of manufacturing a stent device includes a process of preparing a jig 500 having a cylindrical shaft 502, and a braiding process of winding at least one stent wire 504 from a proximal end of the shaft 502 to a distal end of the shaft 502 in a spiral around a longitudinal axis of the shaft 502. The jig 500 has a plurality of pins 506 that are attached to the outer periphery of the shaft 502, and holes are formed at transition points on the outer periphery of the shaft 502 for inserting the pins 506. The holes in the shaft 502 are located at the intersection of a plurality of circumferential dividing lines that extend in the longitudinal direction of the shaft 502 and equally divide the circumference of the shaft 502 into a plurality of pieces, and a plurality of length dividing lines that extend in the circumferential direction of the shaft 502 and equally divide the length of the shaft 502 into a plurality of portions. In the process of preparing the jig 500, a pin 506 is attached to each hole of the shaft 502. The multiple pins 506 attached to the holes are arranged along a spiral path around the longitudinal axis of the shaft 502.

During the braiding process, one end of the stent wire 504 is secured to an anchor pin 508, and the stent wire 504 is extended from the anchor pin 508 to the starting pin 506a, which is the nearest pin located on the length division line. The stent wire 504 is extended in the circumferential direction of the shaft 502 from the starting pin 506a and wound in a zigzag manner around the longitudinal axis of the shaft 502. This forms a plurality of wound stent wires 504. At this time, the stent wire 504 is extended in a zigzag manner in the circumferential direction while alternately passing through pins 506 on one length division line and pins 506 on other length division lines adjacent to the distal side of one length division line. This forms the peak on the pin 506 on one length division line and the valley on the pin 506 on the other length division line.

Figure 6:
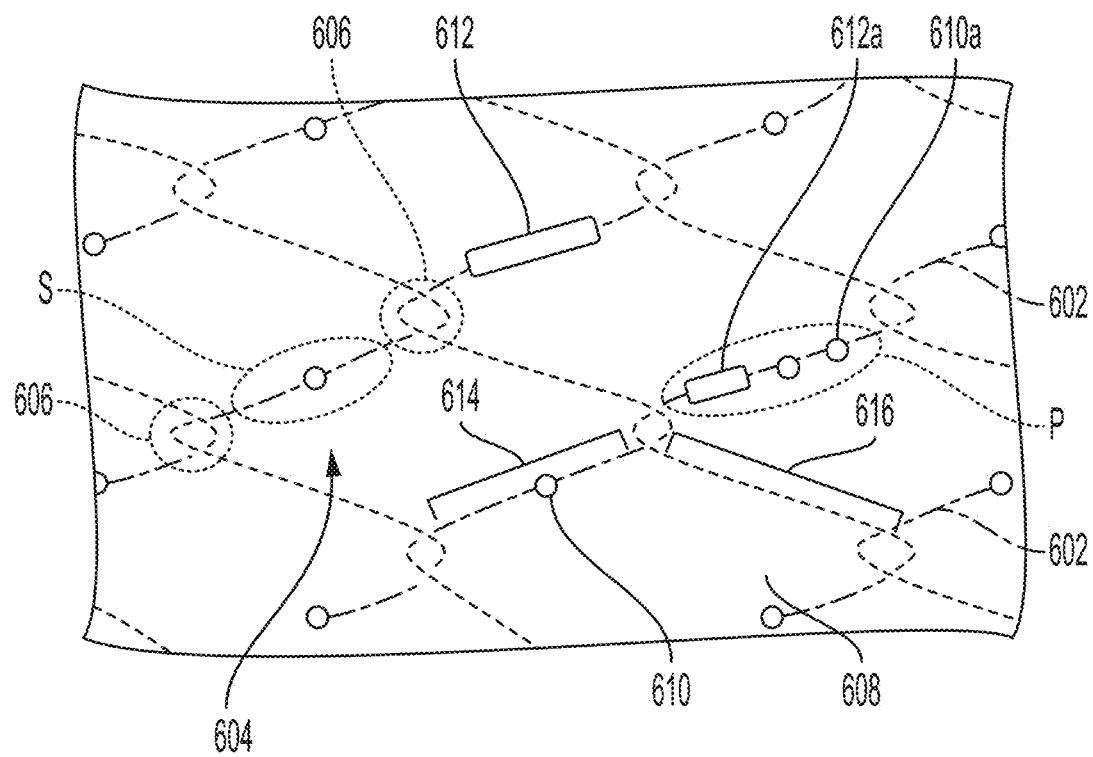
FIG. 6 is a magnified schematic view of embodiments of a stent body and showing aspects of the stent wires.

FIG. 6 illustrates a pattern of the stent wires comprising the stent body of the stent device 104. As disclosed in FIG. 6, the stent wires 602 are interchangeably woven to form cells enclosed by the stent wires 602, such as stent cell 604. The stent wires 602 are entangled at interlocking structures 606, which serves to ease axial force, which is the force for the stent device 104 to return to the original straight position upon being bent. The interlocking structures 606 in FIG. 6 illustrates a primary interlocking structure similar to interlocking 414 shown in FIG. 4, but alternatively may be a secondary interlocking structure, such as an intersection similar to intersection 314 shown in FIG. 3. In FIG. 6, the area annotated with slanted lines represents the stent cover 608, which is connected to the stent wires 602 of the stent body of the stent device 104 through the bonding points 610. The bonding points 610 may be a discreet location, such as a circular or square point, or can be an extended portion, such as bonding portion 612 which has a length dimension that extends along a length of a stent wire 602. The extended portion of the bonding portion 612 has the effect of increasing the fixation of the stent cover 608 to the stent wires 602, but may increase the axial force of the stent device 104. The extended portion of the bonding portion 612 may cover 70% to 90% of one or more stent wires between adjacent interlocking structures 606. The bonding points 610 and bonding portions 612 are located on the stent wires 602 away from and between the interlocking structures 606 (whether primary interlocking structures or secondary interlocking structures). Between interlocking structures 606, there may be a single bonding point 610 or bonding portion 612 (see, e.g. region S in FIG. 6) or there may be a plurality of bonding point 610 or bonding portion 612 (see, e.g. region P in FIG. 6).

The bonding points 610 and bonding portions 612 are located away from the interlocking structures 606 to avoid the interlocking structures 606 being locked in position, which would result in an increase of the axial force, and also negatively affect the flexibility of the stent device 104. Because the bonding points 610 and bonding portions 612 are located only at the stent wires 602 away from the interlocking structures 606, the stent cover 608 and the stent wires 602 may freely move to provide flexibility, without the interlocking structures 606 being locked or limited in their movement during stent flexion or when the stent device 104 is bent. In other words, because the stent wires 602 may freely move together with the bonded stent cover 608, the sliding of the stent wires 602 at the interlocking structures 606 is not hindered, resulting in continuous bending capability and flexibility of the stent device 104.

Furthermore, the bonding points 610 and bonding portions 612 are located on the portions of the stent wires 602 which are closer to the stent cover 608. Because the stent wires 602 are woven together through the interlocking structures 606, the stent wires 602 would be separated into portions forming an inner wire structure 614 and portions forming an outer wire structure 616. Structurally, when viewed in axial cross-section, the portions forming the inner wire structure 614 and the portions forming the outer wire structure 616 are at different radial distances from the longitudinal axis of the stent device, with the portions forming the inner wire structure 614 being radially inward from the portions forming the outer wire structure 616, In FIG. 6, because the stent cover 608 is placed in the inner lumen of the stent device 104, i.e., on the inner surface of the stent device 104, the inner wire structure 614 would be closer to the stent cover 608. Thus, the bonding points 610 and bonding portions 612 would be located on the inner wire structure 614. In contrast, in the case where the stent cover 608 is placed on the outer surface of the stent device 104, the outer wire structure 616 would be closer to the stent cover 608. Thus, the bonding points 610 and bonding portions 612 would be located on the outer wire structure 616.

The stent cover 608 may be made from PTFE films or other polymer films such as silicone or polyurethane, as well as composite film created through lamination. Furthermore, porous ePTFE films may be used to increase the flexibility and elasticity of the film may be more preferable in accordance to usage. The stent cover 608 and the stent device 104 may be bonded by heat welding. In addition to heat welding, adhesion, thread binding, sealing, and other bonding methods compatible with the stent cover 608 may be used.

Figure 7:
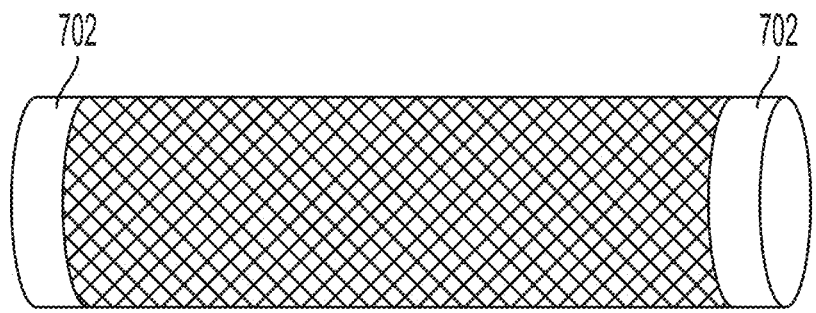
FIG. 7 schematically illustrates a covered stent device with a stent cover attached at the inner lumen of the stent device with excess stent cover folded back and welded together.

FIG. 7 illustrates the stent device 104 with a stent cover 608 attached from the inner lumen through multiple bonding points 610 or bonding portions 612. Because the stent cover 608 is attached from the inner lumen of the stent device 104, the stent wires 602 are exposed to the space exterior to the stent device 104. The stent cover 608 covers the entire inner surface of the stent device 104, and the excess portions (such as at locations 702) of the stent cover 608 at both ends maybe folded back to cover the outer surface of the stent device 104. As a separate embodiment, another set of stent covers with a similar diameter and shorter lengths (e.g. 10 mm or less, preferably 3 to 5 mm) may be placed at outer surfaces of both ends of the stent device 104. The stent cover at both ends of the stent device 104 goes through bonding process described above, attaching the inner stent cover to the outer stent cover directly at the stent cells 604 and surrounding the stent wires 602. The so called "entire-surface fixing" can serve to fix the stent cover 608 firmly to both ends of the stent device 104. The length of the entire-surface fixing at both ends preferably extends 10 mm or less, more preferably 3 to 5 mm in the longitudinal direction of the stent device 104. If present, the entire-surface fixing can be in the same location as the folded back, excess portions at the ends of the stent device 104 (e.g., locations 702). Also, as a separate embodiment, the stent cover 608 may not cover the entire inner lumen or outer surface of the stent device 104, and may only cover only certain portions of the inner lumen and/or outer surface of the stent device 104.

Although not shown in the figures, in alternative embodiments the stent cover 608 may cover the entire outer surface of the stent device 104, and the excess portions of the stent cover 608 at both ends maybe folded back to cover the inner lumens of the stent device 104. As a separate embodiment, another set of stent covers with a similar diameter and shorter lengths (e.g. 10 mm or less, preferably 3 to 5 mm) may be placed at the inner lumen of both ends of the stent device 104. The stent cover at both ends of the stent device 104 goes through bonding process described above, attaching the outer stent cover to the inner stent cover directly at the stent cells 604 and surrounding the stent wires 602. The so called "entire-surface fixing" would serve to fix the stent cover 608 firmly to both ends of the stent device 104. The length of the entire-surface fixing at both ends preferably extends 10 mm or less, more preferably 3 to 5 mm in the longitudinal direction of the stent device 104.

FIG. 8A is a schematic representation of a magnified portion of a stent body of a stent device 104 formed with stent wires 602 and showing interlocking structures 606 and bonding points 610 (represented by solid dots). A stent cover 608 (for clarity, not shown in FIG. 8A) covers the entirety of the magnified portion of the shown stent body from the inner lumen side. The stent wires 602 include inner wire portion 614 and outer wire portion 616 in accordance to the weave of the stent wires 602 and the vicinity to the inner lumen 802 or the exterior space 804 as further described in FIGS. 8B and 8C.

FIG. 8B is a schematic representation of a portion of an axial cross-sectional view taken at A to A' illustrated in FIG. 8A and FIG. 8C is a schematic representation of a portion of a cross-sectional view taken at B to B' illustrated in FIG. 8A. As illustrated in FIGS. 8B and 8C, the stent cover 608 is attached to the stent body of stent device 104 from the inner lumen 802 and the stent wires 602 and bonding points 610 are exposed to the exterior space 804 of the stent device 104. The stent wire 602a is part of inner wire portion 614 and is located radially inward relative to stent wire 602b, which is part of the outer wire portion 616. As part of the inner wire portion 614, stent wire 602a is positioned at a first distance from the stent cover 608 and, as part of the outer wire portion 616, the stent wire 602b is positioned at a second distance from the stent cover 608, the second distance being larger than the first distance, meaning that stent wire 602b is farther away from the stent cover 608 as compared to stent wire 602a. Thus, bonding points 610 are formed at stent wires 602a of inner wire portion 614 and not at stent wires 602b of the outer wire portion 616.

Figure 9A:
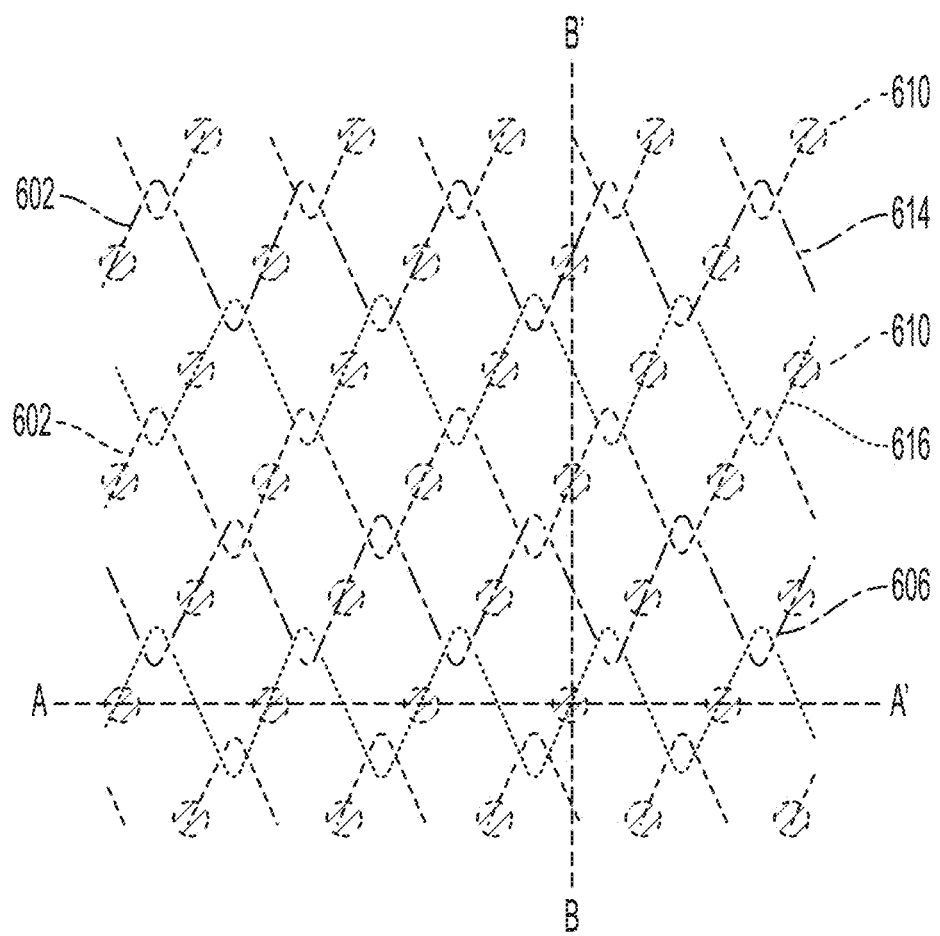
FIGS. 9A to 9C are magnified schematic views of embodiments of a stent body and showing aspects of the stent wires.
Figure 9B:
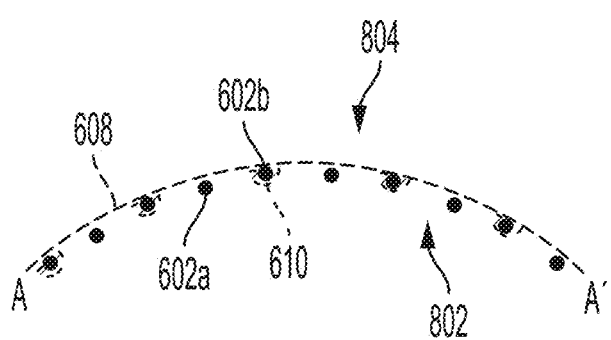
Figure 9C:
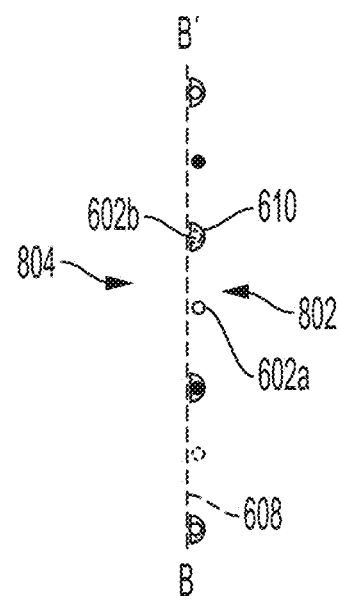

FIG. 9A is a schematic representation of a magnified portion of a stent body of a stent device 104 formed with stent wires 602 and interlocking structures 606, bonding points 610 (represented by solid dots). A stent cover 608 (for clarity, not shown in FIG. 9A) covers the entirety of the magnified portion of the shown stent body from the outer surface. The stent wires 602 include inner wire portion 614 and outer wire portion 616 in accordance to the weave of the stent wires 602 and the vicinity to the inner lumen 802 or the exterior space 804 as further described in FIGS. 9B and 9C FIG. 9B is a schematic representation of an axial cross-sectional view at A to A' illustrated in FIG. 9A and FIG. 9C is a schematic representation of a portion of a cross-sectional view taken at B to B' illustrated in FIG. 9A. As illustrated in FIGS. 9B and 9C, the stent cover 608 is attached to the stent body of the stent device 104 from the exterior space 804 and the stent wires 602 and bonding points 610 are exposed to the inner lumen 802 of the stent device 104. The stent wire 602b is part of the outer wire portion 616 is located radially outward relative to stent wire 602a, which is part of the inner wire portion 614. As part of the inner wire portion 614, stent wire 602a is positioned at a first distance from the stent cover 608 and, as part of the outer wire portion 616, the stent wire 602b is positioned at a second distance from the stent cover 608, the second distance being larger than the first distance, meaning that stent wire 602b is farther away from the stent cover 608 as compared to stent wire 602a. Thus, bonding points 610 are formed at stent wires 602b of outer wire portion 616 and not at stent wires 602a of the inner wire portion 614.

Figure 10A:
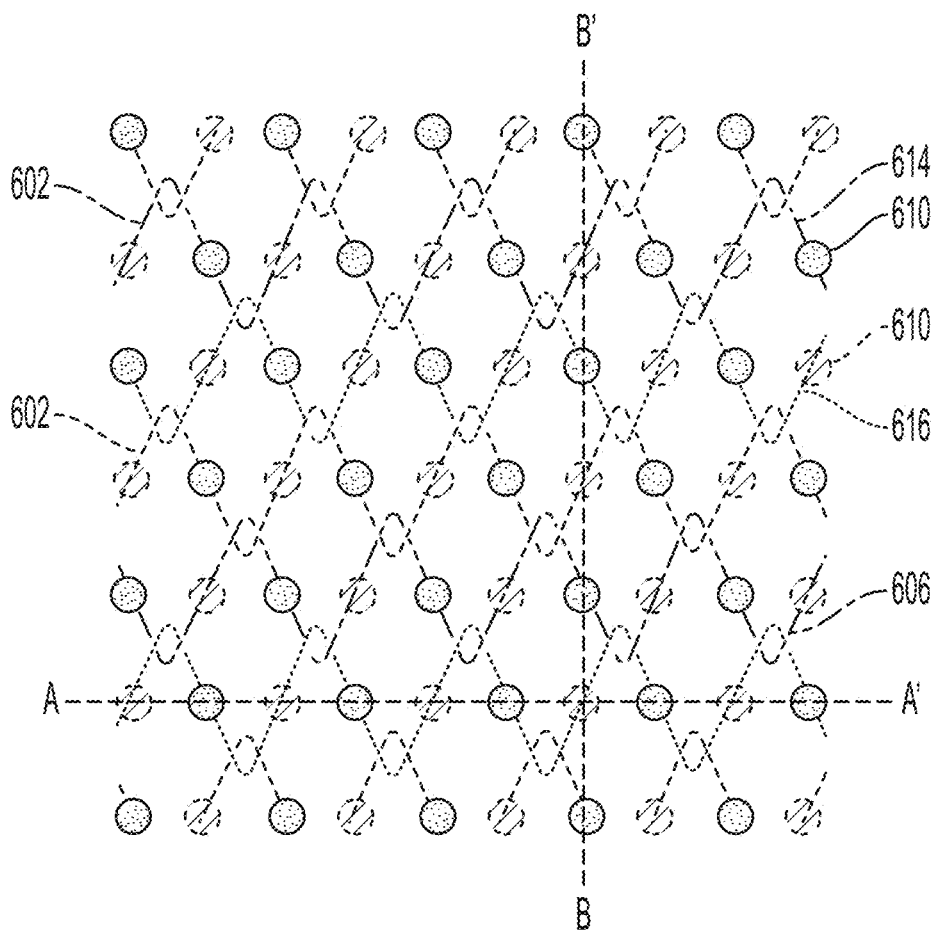
FIGS. 10A to 10C are magnified schematic views of embodiments of a stent body and showing aspects of the stent wires.

FIG. 10A is a schematic representation of a magnified portion of a stent body of a stent device 104 formed with stent wires 602 and showing interlocking structures 606 and bonding points 610 (represented by solid dots). A stent cover (for clarity, not shown in FIG. 10A), includes a first stent cover portion 608a covering the entirety of the magnified portion of the stent body from the inner lumen side and a second stent cover portion 608b covering the entirety of the magnified portion of the stent body from the outer surface of the stent device 104. The stent wires 602 include inner wire portion 614 and outer wire portion 616 in accordance to the weave of the stent wires 602 and the vicinity to the inner lumen 802 or the exterior space 804 further described in FIGS. 10B and 10C.

Figure 10B:
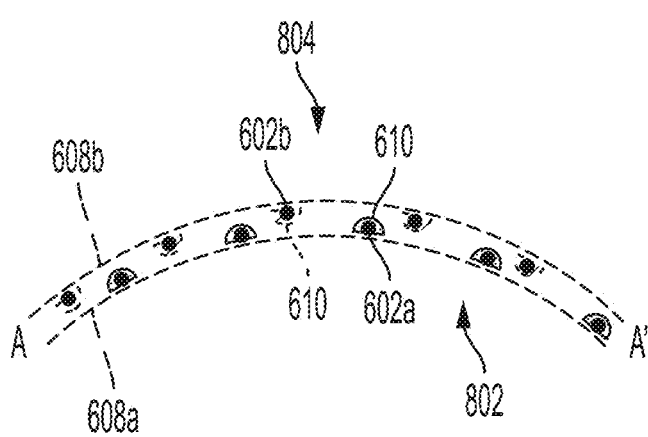
Figure 10C:
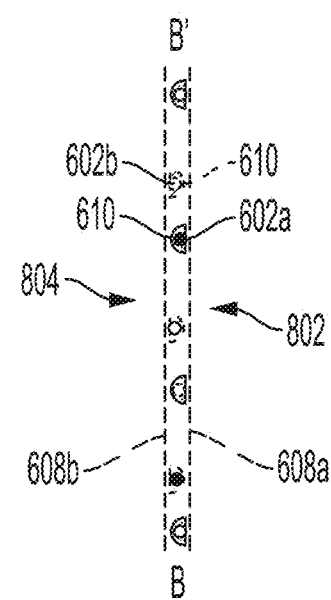

FIG. 10B is a schematic representation of a portion of an axial cross-sectional view taken at A to A' illustrated in FIG. 10A and FIG. 10C is a schematic representation of a portion of an axial cross-sectional view taken at B to B' illustrated in FIG. 10A. As illustrated in FIGS. 10B and 10C, the stent cover 608 is attached to the stent body of the stent device 104 from both the inner lumen 802 and the exterior space 804. In particular, the first stent cover portion 608a is attached to the stent body of the stent device 104 from the inner lumen 802 and the second stent cover portion 608b is attached to the stent body of the stent device 104 from the exterior space 804. The stent wire 602a that is part of the inner wire portion 614 and the stent wire 602b that is part of the outer wire portion 616 are both positioned in the vicinity of respective portions of the stent cover 608, and thus, the stent device 104 are bonded to the respective stent covers 608a, 608b through bonding points 610 through both stent wires 602a of inner wire portion 614 and the stent wire 602b of outer wire portion 616. The bond between the stent wire 602a that is part of the inner wire portion 614 and the first stent cover portion 608a that is attached to the stent body of the stent device 104 from the inner lumen 802 is similar to that shown and described with FIGS. 8A to 8C. The bond between the stent wire 602b that is part of the outer wire portion 616 and the second stent cover portion 608b that is attached to the stent body of the stent device 104 from the exterior space 804 is similar to that shown and described with FIGS. 9A to 9C.

Figure 11:
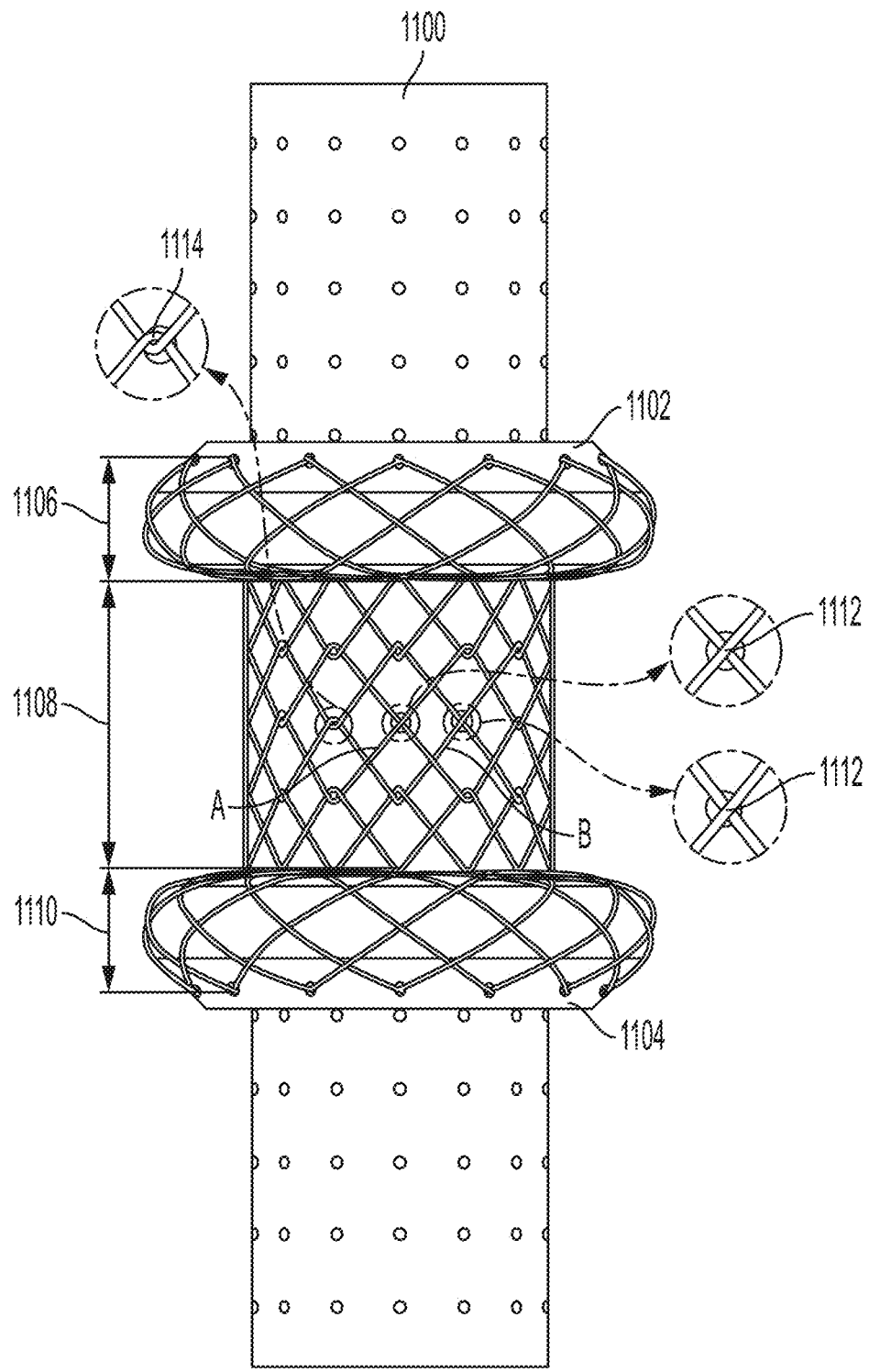
FIGS. 11 and 12 show alternative stent devices that can incorporate embodiments of the disclosed stent cover.

Embodiments of the stent cover disclosed herein can be utilized as stent covers in any of the variously known stent devices. For example, FIG. 11 schematically illustrates a first alternative stent device, such as is disclosed in the related art (U.S. Pat. No. 10,349,944, the entire contents of which are incorporated herein by reference), to which a stent cover can be attached. The attached stent cover can be consistent with the embodiments disclosed herein. In the first alternative stent device, the first stent wire A and second stent wire B are woven around the jig 1100 including an upper head formation member 1102 and a lower head formation member 1104. The woven stent device comprises of upper head 1106, body 1108, and lower head 1110, and includes intersection portions 1112 and ring-shaped portions 1114. The stent cover 608 may be attached to the first alternative stent body of the stent device from one or both of the inner lumen and the exterior space, in substantially same manner as disclosed in FIGS. 8A to C, 9A to C, and 10A to C. For example, the first stent cover portion 608a is attached to the stent body of the first alternative stent device from the inner lumen and the second stent cover portion 608b may be attached to the stent body of the first alternative stent device from the exterior space. The stent wire that is part of the equivalent of inner wire portion 614 and the stent wire that is part of the equivalent of outer wire portion 616 are both positioned in the vicinity of respective portions of the stent cover 608, and thus, the first alternative stent device is bonded to the respective stent covers through equivalents of bonding points 610. The bond between the stent wire that is part of the equivalents of inner wire portion 614 and the first stent cover portion 608a that is attached to the stent body of the first alternative stent device from the inner lumen is similar to that shown and described with FIGS. 8A to 8C. The bond between the stent wire that is part of the equivalents of outer wire portion 616 and the second stent cover portion 608b that is attached to the stent body of the first alternative stent device from the exterior space is similar to that shown and described with FIGS. 9A to 9C. In alternative embodiments, when the stent cover is attached from one of the inner lumen and the exterior space, the above description for the attachment of the stent cover from just the one side is applicable.

Figure 12:
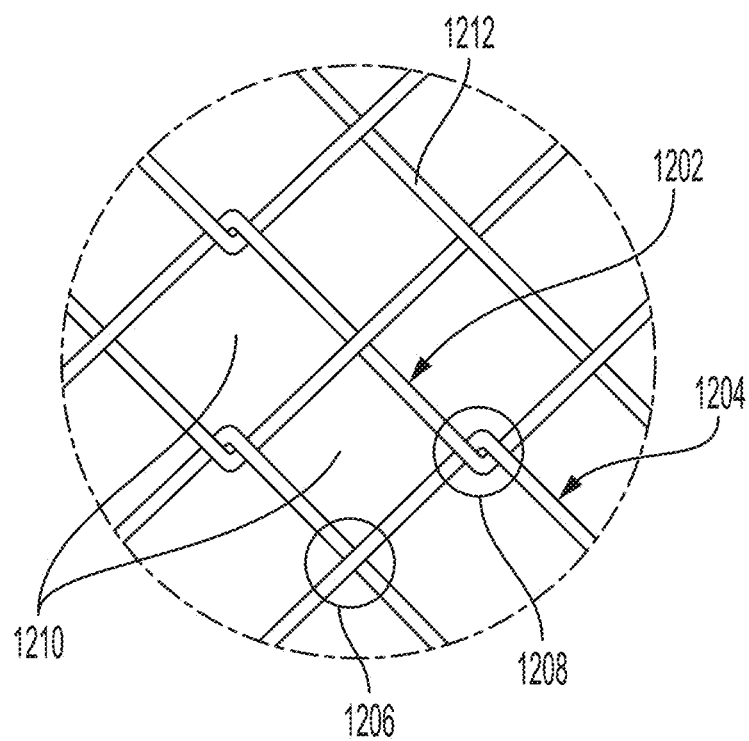
Figure 13:
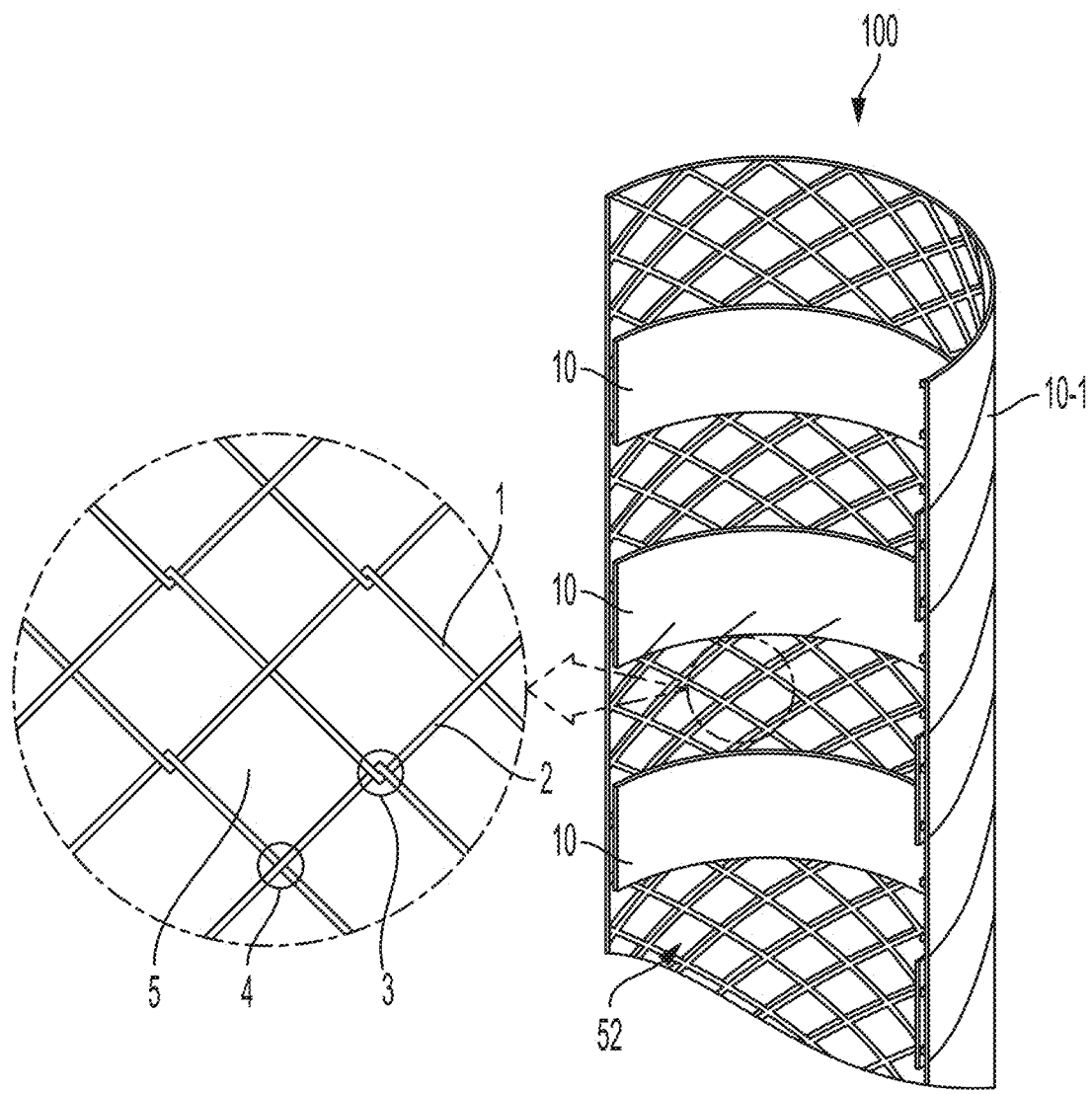
FIGS. 13 and 14 show related art stent devices.
Figure 14:
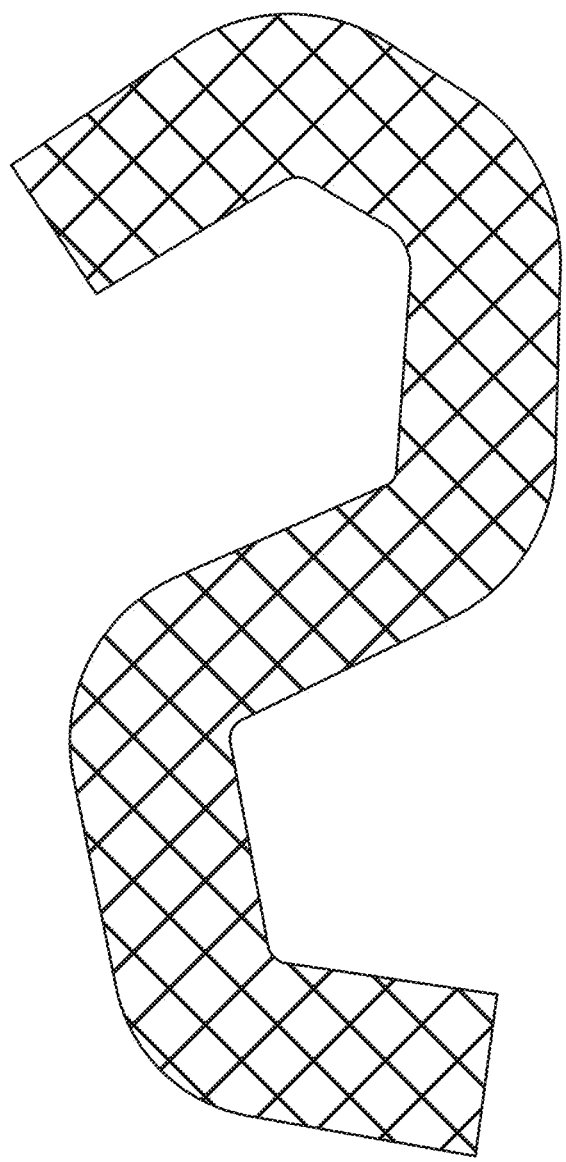

Also for example, FIG. 12 schematically illustrates a second alternative stent device, such as is disclosed in the related art (U.S. Pat. No. 8,313,522, the entire contents of which are incorporated herein by reference), to which a stent cover can be attached. The attached stent cover can be consistent with the embodiments disclosed herein. In the second alternative stent device, the first and second superelastic shape memory alloy wires 1202 and 1204 are woven to form the second alternative stent device that includes intersection portions 1206 and interlocking portions 1208, leaving plurality of rhombic spaces 1210 therebetween. Furthermore, the downward extension part 1212 of the first wire 1202 serves to restrain the longitudinal contraction or extension of the second alternative stent device. The stent cover 608 may be attached to the second alternative stent body of the stent device from one or both of the inner lumen and the exterior space, in substantially same manner as disclosed in FIGS. 8A to C, 9A to C, and 10A to C. For example, the first stent cover portion 608a is attached to the stent body of the second alternative stent device from the inner lumen and the second stent cover portion 608b may be attached to the stent body of the second alternative stent device from the exterior space. The stent wire that is part of the equivalent of inner wire portion 614 and the stent wire that is part of the equivalent of outer wire portion 616 are both positioned in the vicinity of respective portions of the stent cover 608, and thus, the second alternative stent device is bonded to the respective stent covers through equivalents of bonding points 610. The bond between the stent wire that is part of the equivalents of inner wire portion 614 and the first stent cover portion 608a that is attached to the stent body of the second alternative stent device from the inner lumen is similar to that shown and described with FIGS. 8A to 8C. The bond between the stent wire that is part of the equivalents of outer wire portion 616 and the second stent cover portion 608b that is attached to the stent body of the second alternative stent device from the exterior space is similar to that shown and described with FIGS. 9A to 9C. In alternative embodiments, when the stent cover is attached from one of the inner lumen and the exterior space, the above description for the attachment of the stent cover from just the one side is applicable.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A covered stent device, comprising:
one or more stent wires forming a stent body, wherein the stent body includes:
a plurality of cross over points forming a plurality of interlocking open cells in which each open cell includes a perimeter defined by a plurality of portions of the one or more stent wires and enclosing a cell void space, and
an inner wire structure formed by a first portion of the plurality of portions of the one or more stent wires and an outer wire structure formed by a second portion of the plurality of portions of the one or more stent wires; and
at least one stent cover,
wherein the first portion of the plurality of portions of the one or more stent wires forming the inner wire structure are at a first radial distance from a longitudinal axis of the stent device and the second portions of the one or more stent wires forming the outer wire structure are at a second radial distance from the longitudinal axis of the stent device, the first distance less than the second distance,
wherein the perimeter of each open cell includes a plurality of bonding locations, and
wherein:
a first part of the at least one stent cover is located radially inward of the stent body and is attached to the stent body only at the plurality of bonding locations located on the inner wire structure, and
a second part of the at least one stent cover is located radially outward of the stent body and is attached to the stent body only at the plurality of bonding locations located on the outer wire structure.

2. The covered stent device according to claim 1, wherein a single bonding location of the plurality of bonding locations is located between an adjacent two of the plurality of cross over points.

3. The covered stent device according to claim 1, wherein multiple bonding locations of the plurality of bonding locations are located between an adjacent two of the plurality of cross over points.

4. The covered stent device according to claim 1, wherein the plurality of bonding locations are present on up to 80% of a total length of the plurality of portions of the one or more stent wires defining the perimeter and that extend between adjacent cross over points.

5. The covered stent device according to claim 1, wherein the first part of the at least one stent cover is an inner stent cover, and wherein the inner stent cover extends an entire axial length of the stent body.

6. The covered stent device according to claim 1, wherein the first part of the at least one stent cover is an inner stent cover, and wherein the inner stent cover is folded back to cover an end portion of an outer surface of the stent body.

7. The covered stent device according to claim 1, wherein the second part of the at least one stent cover is an outer stent cover, and wherein the outer stent cover extends an entire axial length of the stent body.

8. The covered stent device according to claim 1, wherein the second part of the at least one stent cover is an outer stent cover, and wherein the outer stent cover is folded back to cover an end portion of an inner lumen surface of the stent body.

9. The covered stent device according to claim 1, wherein the plurality of cross over points include a primary interlocking structure.

10. The covered stent device according to claim 1, wherein the plurality of cross over points include a secondary interlocking structure.

11. A stent delivery system, comprising:
a tip;
the covered stent device according to claim 1;
a double layered sheath having a sheath axial length and configured to carry the covered stent device from a first position along the sheath axial length to a second position along the sheath axial length; and
a handle for removing the stent device from the double layered sheath.

12. The covered stent device according to claim 1, wherein the plurality of bonding locations include a plurality of bonding points.

13. The covered stent device according to claim 1, wherein the plurality of bonding locations include a plurality of bonding portions.

14. The covered stent device according to claim 1, wherein the plurality of bonding locations include a plurality of bonding points and a plurality of bonding portions.

15. A covered stent device, comprising:
one or more stent wires forming a stent body, wherein the stent body includes:
a plurality of cross over points forming a plurality of interlocking open cells in which each open cell includes a perimeter defined by a plurality of portions of the one or more stent wires and enclosing a cell void space, and
an inner wire structure formed by a first portion of the plurality of portions of the one or more stent wires and an outer wire structure formed by a second portion of the plurality of portions of the one or more stent wires; and
at least one stent cover,
wherein the first portion of the plurality of portions of the one or more stent wires forming the inner wire structure are at a first radial distance from a longitudinal axis of the stent device and the second portions of the one or more stent wires forming the outer wire structure are at a second radial distance from the longitudinal axis of the stent device, the first distance less than the second distance,
wherein the perimeter of each open cell includes a plurality of bonding locations, and
wherein:
a first stent cover of the at least one stent cover is located radially inward of the stent body and is attached to the stent body only at the plurality of bonding locations located on the inner wire structure, and
a second stent cover of the at least one stent cover is located radially outward of the stent body and is attached to the stent body only at the plurality of bonding locations located on the outer wire structure.

16. The covered stent device according to claim 15, wherein at least one of the first stent cover and the second stent cover extends an entire axial length of the stent body.

17. The covered stent device according to claim 15, wherein both the first stent cover and the second stent cover extend an entire axial length of the stent body.

18. The covered stent device according to claim 15, wherein the first stent cover and the second stent cover are bonded together at the cell void space of the plurality of interlocking open cells.

19. The covered stent device according to claim 15, wherein the plurality of cross over points include a primary interlocking structure.

20. The covered stent device according to claim 15, wherein the plurality of cross over points include a secondary interlocking structure.

21. The covered stent device according to claim 15, wherein the plurality of bonding locations include a plurality of bonding portions.

22. The covered stent device according to claim 15, wherein the plurality of bonding locations include a plurality of bonding points and a plurality of bonding portions.

23. A stent delivery system, comprising:
a tip;
the covered stent device according to claim 15;
a double layered sheath having a sheath axial length and configured to carry the covered stent device from a first position along the sheath axial length to a second position along the sheath axial length; and
a handle for removing the stent device from the double layered sheath.

* * * * *